(12) United States Patent
Monstadt et al.

(10) Patent No.: US 9,737,318 B2
(45) Date of Patent: Aug. 22, 2017

(54) THROMBECTOMY DEVICE

(75) Inventors: Hermann Monstadt, Bochum (DE); Ralf Hannes, Dortmund (DE); Jorg Ascherfeld, Hattingen (DE)

(73) Assignee: Phenox GmbH, Bochum (DE)

( * ) Notice: Subject to any disclaimer, the term of this patent is extended or adjusted under 35 U.S.C. 154(b) by 0 days.

(21) Appl. No.: 13/885,514

(22) PCT Filed: Nov. 18, 2011

(86) PCT No.: PCT/EP2011/005817
§ 371 (c)(1),
(2), (4) Date: Jul. 17, 2013

(87) PCT Pub. No.: WO2012/065748
PCT Pub. Date: May 24, 2012

(65) Prior Publication Data
US 2013/0296916 A1    Nov. 7, 2013

(30) Foreign Application Priority Data

Nov. 19, 2010    (DE) .................. 10 2010 051 740

(51) Int. Cl.
*A61M 29/00*    (2006.01)
*A61B 17/221*    (2006.01)
(Continued)

(52) U.S. Cl.
CPC .... *A61B 17/221* (2013.01); *A61B 17/320725* (2013.01); *A61F 2/915* (2013.01); *A61F 2002/825* (2013.01)

(58) Field of Classification Search
CPC .......... A61B 17/221; A61B 17/320725; A61B 17/32075; A61B 17/12113; A61B 17/11; A61B 17/12045; A61B 2017/2215; A61B 2017/22034; A61B 2017/22094; A61B 2017/12063; A61B 2017/00292; A61F 2002/825; A61F 2/915; A61F 2002/91558; A61F 2002/018; A61F 2002/91541;
(Continued)

(56) References Cited

U.S. PATENT DOCUMENTS 5,618,299 A * 4/1997 Khosravi et al. .............. 623/1.2
8,945,161 B2    2/2015 Miloslavski et al.
(Continued)

FOREIGN PATENT DOCUMENTS

WO    WO 2009105710 A1 *  8/2009

OTHER PUBLICATIONS

Notice of Allowance issued Apr. 10, 2015 in connection with U.S. Appl. No. 14/000,658, filed Oct. 28, 2013.

*Primary Examiner* — Katherine M Shi
*Assistant Examiner* — Mohamed Gabr
(74) *Attorney, Agent, or Firm* — Berliner & Associates

(57) ABSTRACT

The invention relates to a thrombectomy device having a substantially cylindrical stent structure (1) comprised of a plurality of meshes (3, 4) and also two connectors (5, 5') that are disposed at different meshes (3) at the proximal end of the stent structure (1). The device also has a guide wire (12), which comprises a coupling element (11) to which the connectors (5, 5') are coupled, and a slit (7), which extends helically over the shell face (8) of the stent structure (1), and a tensioning clip (9) that spans the slit (7) at the proximal end.

13 Claims, 3 Drawing Sheets

(51) Int. Cl.
  *A61B 17/3207* (2006.01)
  *A61F 2/915* (2013.01)
  *A61F 2/82* (2013.01)

(58) Field of Classification Search
  CPC ........ A61F 2002/016; A61F 2/91; A61F 2/95;
    A61F 2/013; A61F 2/92; A61F 2/82;
    A61F 2/88; A61F 2/90; A61F 2/856;
    A61F 2/966; A61F 2230/0008; A61F
    2230/0069; A61F 2230/0091
  USPC ...... 623/1.11–1.16, 1.2, 1.46, 1.19; 606/108,
    606/191, 194, 198, 200
  See application file for complete search history.

(56) References Cited

U.S. PATENT DOCUMENTS

| | | |
|---|---|---|
| 2009/0198269 A1 | 8/2009 | Hannes et al. |
| 2009/0306702 A1 | 12/2009 | Miloslavski et al. |
| 2010/0152834 A1 | 6/2010 | Hannes et al. |
| 2011/0009875 A1* | 1/2011 | Grandfield et al. .......... 606/127 |
| 2011/0009940 A1* | 1/2011 | Grandfield ................ A61F 2/90 623/1.11 |
| 2011/0060359 A1 | 3/2011 | Hannes et al. |
| 2011/0184451 A1 | 7/2011 | Sahl |
| 2011/0224707 A1 | 9/2011 | Miloslavski et al. |
| 2011/0238148 A1 | 9/2011 | Monstadt et al. |
| 2011/0264193 A1* | 10/2011 | Abunassar .................. 623/1.15 |
| 2013/0138198 A1 | 5/2013 | Aporta et al. |
| 2013/0211492 A1 | 8/2013 | Schneider et al. |
| 2014/0058420 A1 | 2/2014 | Hannes et al. |
| 2014/0058498 A1 | 2/2014 | Hannes et al. |
| 2014/0343595 A1 | 11/2014 | Monstadt et al. |

* cited by examiner

THROMBECTOMY DEVICE

The invention relates to a thrombectomy device having a substantially cylindrical stent structure, which is comprised of a multiplicity of meshes and two connectors that are arranged on different meshes at the proximal end of the stent structure, and comprising a guide wire which has a coupling element which the connectors are coupled to. The thrombectomy device is especially destined for removing thrombi in the cerebral area like those frequently encountered with apoplectic strokes, said removal to be performed in a way that is gentle to a patient and reliable.

Thromboembolic diseases such as myocardial infarction, pulmonary embolism, peripheral thrombosis, organ embolism, etc. are typically triggered by a thromboembolus (hereinafter briefly referred to as thrombus), i.e. a viscoelastic blood clot composed of blood platelets, fibrinogen, clotting factors, etc., which has become stuck in a blood vessel and occludes it entirely or partly. An occlusion of organ arteries leads to an interruption in the supply of the dependent tissue with oxygen and nutrients. The disturbance of the functional metabolism accompanied by a loss of function is followed by a failure of the structural metabolism within a short period of time, entailing a destruction of the affected tissue (infarct). The most common organs affected thereby with human beings are the heart and the brain. But such changes also affect limb arteries and pulmonary arteries. Venous thrombosis and thromboembolic occlusion frequently appear in leg and pelvic veins, too. The pathology of thrombotic occlusion of an intracranial sinus may cause severe intracerebral hemorrhage due to a disturbance in the venous drainage of the brain tissue.

In view of the severity of disease patterns triggered by thromboembolism and considering the frequency of these diseases, there are various techniques known from prior art and developed for dissolving or removal of thrombi.

For example, it is known from prior art treating such patients with thrombolytic means such as streptokinase or urikinase or with anticoagulants serving for thrombolysis or containment of thrombus growth. As these treatment methods in most cases are time-consuming, they are often combined with methods serving for medical diminution or removal of the thrombus and embolus, respectively.

Apart from open surgical interventions, transluminal and/or endovascular catheter-guided interventional therapy methods are increasingly applied in state-of-the-art technology because these methods are less invasive. For example, it is known from prior art to remove a thrombus by means of suction catheters generating a negative pressure or mechanically by means of catheters equipped with capturing cages, helixes, hooks, or the like, from a patient's body. For reference, vide U.S. Pat. No. 6,215,089 B1; U.S. Pat. No. 5,171,233 A1, Thomas E. Meier at al., Stroke 2002 (9) 2232.

A drawback of thrombolytic treatment methods lies in that they are rarely successful once the available time frame has elapsed. Even those well-known transluminal devices frequently are unable to remove a thrombus completely, there also being a risk in that the thrombus or fragments thereof are released and entrained as freight in the blood stream to smaller vessels where they are harder to reach and treat. Furthermore, owing to their dimensions and/or low flexibility, prior art devices are merely insufficiently able to remove thrombi, especially from smaller or severely wound vessels like those in brain.

Known from WO 2004/008991 A1 is a medical implant in form of an open stent which is intended for treatment of aneurysms and other vascular malformations. This implant is guided by the aid of a guide wire to the point of application and detached there. It was proposed to implement this combination of an implant and a guide wire for extraction of thrombi, with a detachment of the implant part from the guide wire naturally being waived. A drawback of this design comprised of an implant and a guide wire, however, is a relatively low tensile force or spring load. This structure unfolds a not always sufficient shear force on the thrombus sitting in the vessel wall so that residues remain in the vessel. A tie-up to the guide wire via a tapering structure (teardrop) in particular leads to a streamlining of the proximal region of the structure under tension which opposes the efficiency of this structure.

Considering the drawbacks associated with prior art technology, it now, therefore, is the object of the present invention to provide a device for removal of foreign bodies and thrombi from blood vessels, more particularly a device allowing for removal of thrombi from smaller vessels whilst featuring good maneuverability in severely wound vessels and providing a large active surface.

This objective is inventively achieved by a device of the afore-mentioned kind which is comprised of a slit extending helically across the shell face of the stent structure and which is spanned-over by a tensioning clamp at the proximal end of the stent structure.

The inventive device is comprised of a cylindrical structure like the one encountered in stents, too, having a plurality of meshes. It is connected via two connectors to a guide wire which allows for precise positioning and spotting. At the proximal end, the connectors are arranged in a mesh structure and they terminate in a coupling element which in turn represents the distal end of the guide wire.

The term "proximal" as used herein designates the side facing the doctor performing the treatment, whereas the term "distal" designates the side averted from the doctor, for example the stent structure or the guide wire.

The mesh structure of the stent may be a braided structure, i.e. it may be comprised of single wires, but preferably it is a cut structure, wherein the mesh structure is cut out with a laser from a pipe having a suitable diameter. In general, the material is metal, but plastic material may also be used. It must have adequate elasticity allowing for contraction to the diameter of a commonly applied catheter and which on the other hand permits an expansion to the desired and specified diameter when released from the catheter.

Apart from iron alloys (stainless steel, spring steel) and cobalt-chromium alloys, materials eligible for use as stent materials are especially shape-memory alloys, such as binary nickel titanium alloys (Nitinol), and ternary nickel-titanium-chromium alloys (chromium-endowed alloys). Especially Nitinol is well known for applications in auto-expanding stent structures in a neurovascular range.

The inventive device in principle is a planar, two-dimensional structure which is rolled-up to become a tubular construct having a slit which extends helically over the shell face of the stent structure. This slit may represent a complete helix of 360°, but likewise only a partial helix of approximately 180° or 120°, for example. The shell face of the stent structure gapes widely open in the area of this slit, with the width of the slit at the point of application being determined by the lumen of the vessel, too, because the stent structure once released from the catheter can unfold itself only to the extent permitted by the vessel volume.

In order to fix the stent structure spatially on the one hand and to provide it with a certain tension on the other hand, a tensioning clip extends at the proximal end of the stent structure over the slit. The tensioning clip increases the radial force of the auto-expanding structure, but it also serves for retaining the stent structure edges lying opposite to each other along the slit in their position.

The inventive thrombectomy device may comprise further tensioning clips beyond the proximal tensioning dip in the central and distal area. On using shape-memory materials with adequate pre-tensioning, however, any tensioning clip can be dispensed with.

The inventive thrombectomy device is so applied that it is taken by means of as catheter to the point of application and released there either in the thrombus itself or distally of the thrombus. The device expands in the vessel and adapts itself to the vessel lumen. Either already when clamped on or when retracted, the thrombus material gets caught in the mesh structure and is entrained when the device is retracted into the catheter. Parts of the thrombus adhering to the vessel wall are entrained by the shear effect of the meshes and the edges along the slit. The thrombus is pulled into the catheter and removed with the catheter out of the body.

On extraction of a thrombus, the helically shaped course of the slit extending over the shell face bears a special advantage in that the edges of the stent structure along the slit when subjected to tension migrate along the periphery of the vessel wall. This improves the shear effect. At the same time, due to the helically shaped course, the bending stiffness improves (diminishes) in such a manner that a better adaptation to curvy vessels is feasible. This facilitates both the placement and the extraction of thrombi from complex vascular structures.

The proximal clip improves the radial force curve of the stent structure in the proximal area. In particular, the clip diminishes a slimming-down of the stent structure and of the tensile load as occurring on pulling it into a catheter. At the same time, an additional peeling effect is achieved in the same way as it is practiced by the meshes and edges of the stent structure.

But it is of major importance to improve the clamping force in the proximal area that allows for optimally adapting the stent structure to the vessel lumen. At the same time, the areas of the stents that are separated from each by the slit are prevented from shifting them reciprocally.

In order to allow for unproblematic pulling-in of the stent structure into a catheter, the tensioning clip points to the distal end of the stent structure. This means that the arch of the clip is closed towards the distal position, but towards the proximal position and together with the connectors it forms a sling that converges in the coupling element similarly to the opening of a capturing cage.

In accordance with one variant, the inventive stent structure may be occluded by a mesh structure at the distal end so that thrombotic material gathers therein as in a capturing cage.

As has been stated hereinabove, the inventive stent structure is preferably cut out from a cylindrical tube by the aid of a laser. This allows for providing the individual meshes with a special cross-section, for example a square, rectangular or trapezoidal cross-section. With rectangular or trapezoidal configurations, the small side of the cross-section may lie at the outer face on the one hand and the long side on the other hand. It is preferred that the small side both of the rectangle and especially of the trapezoid points to the vessel will which enables easier penetration of the thrombus into the mesh structure and which allows for good displacement of the thrombus mass on expanding the stent structure.

The connectors arranged at the proximal end of the stent structure lead from the proximal combs lying adjacent to the slit to a coupling element in which they are converged. They are parts of the stent structure and therefore they are made of the same material.

The guide wire of the inventive thrombectomy device is a usual guide wire like the one used for endovascular and particularly for neuroradiological purposes. It terminates distally in the coupling element which in turn accommodates the proximal ends of the connectors.

The coupling element itself may be a simple welding spot in which the guide wire and connector are converged. Furthermore, it may also be a usual coupling element that allows for releasing the cylindrical stent structure which is especially needed if a retrieval is not indicated for medical reasons, for example because it would entail harm to a patient. In this case, the stent structure may remain as a stent in a body and unfold its effect by forming a channel in the thrombus, and the thrombus is pressed by the mesh structure against the vessel wall.

For the latter case, for example, the coupling element is a mechanical coupling element which is suitable of releasing the connectors when leaving the catheter. Numerous systems of this kind have been described in the relevant specialist literature. Also described therein are hydraulic detachment systems. Especially suitable are electrolytic detachment systems wherein an electrolytically corrodible part is dissolved when subjected to electric power, thus cutting the connection between the stent structure and the guide wire. In accordance with a first variant, the coupling element may be configured as such an electrolytically dissolvable part, and in accordance with a second variant the connectors are provided with such a detachment point and/or a separate detachment element which gets dissolved when subjected to the impact of electric power. Suitable for use as detaching elements are pre-corroded stainless steel elements, magnesium elements or cobalt-chromium alloys. Systems of this kind are described in the relevant literature.

On configuring the proximal area of the cylindrical stent structure, preference is given to a short-type connector. The way between the proximal end of the mesh structure and the coupling element should be kept short. On the one hand this will shorten the non-used length of the device and on the other hand it increases the tension in the capture sling formed with the tensioning clip at the proximal end of the structure.

In accordance with a special embodiment, the distal area of the cylindrical stent structure may be widened-up and/or expanded in form of a cone or a trumpet in order to facilitate good adaptation in this area to a vascular lumen. On extracting thrombi from a vessel, it is the largest possible effective range that matters, i.e. the contact of the shell face with the vessel wall. The larger the contact area, the higher is the chance for removing a thrombus completely.

Guide wire and/or stent structure may be provided with markers in the usual manner, which are radiopaque, for example in form of spirals or cuffs or sleeves.

The invention is further elucidated by way of the enclosed drawings, where:

FIG. 4 is a three-dimensional representation of the stent structure of FIG. 3 with a guide wire coupled-on;

Figure 1:
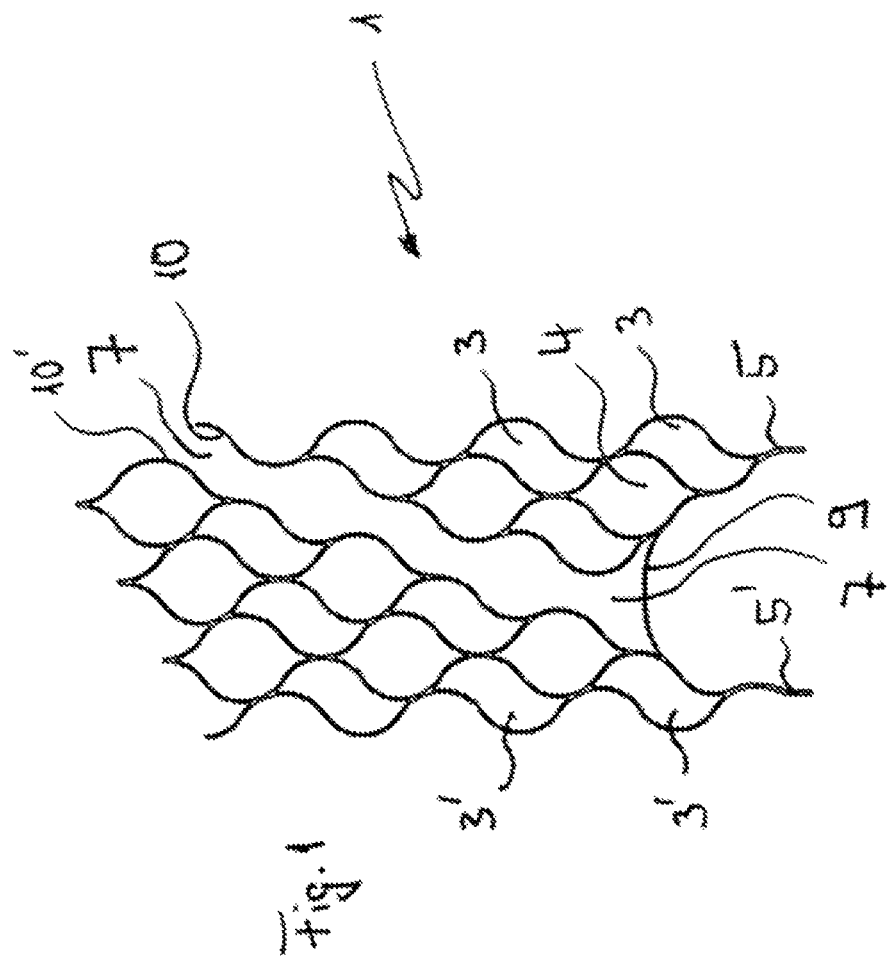
FIG. 1 shows a first variant of the inventive stent structure in a planar, two-dimensional view.
Figure 3:
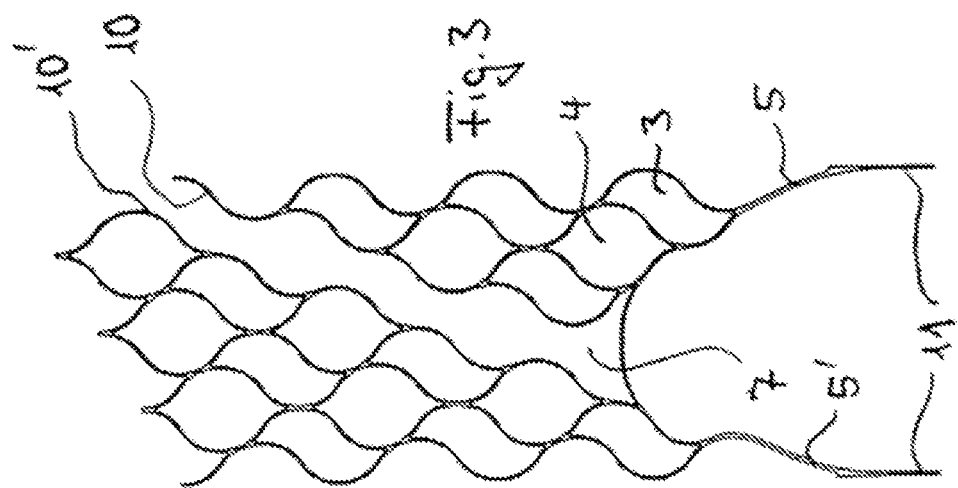
FIG. 3 shows a planar, two-dimensional representation of a second variant of an inventive stent structure.

FIGS. 1 and 3 show two variants of an inventive cylindrical stent structure 1 with the individual meshes 3 and 4 and the connectors 5 and 5'. The meshes 3 and 4 are of two different types, one type (3) having a wave shape, the other type (4) having a bulbous shape with two tips. When co-acting, these two shapes provide the overall structure with both stability and flexibility.

In the planar, two-dimensional representation of FIGS. 1 and 3, a slit or channel 7 extends through the stent structure, said slit or channel being bridged by the tensioning dip 9 at the proximal end of the structure. The slit 7 is confined by the lateral faces 10 and 10' of the mesh structure. The slit 7 does not extend in parallel to the longitudinal axis of the structure, but obliquely to the longitudinal axis which in the three-dimensional is represented as a helically-shaped course along the shell face ((see FIG. 2/4).

Figure 2:
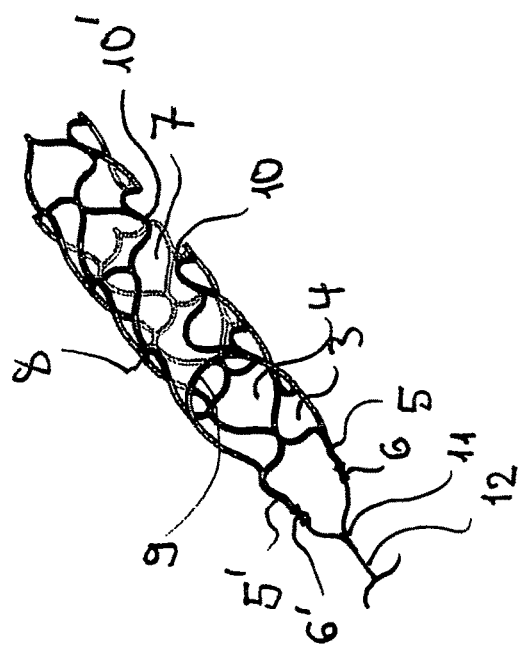
FIG. 2 shows a three dimensional view of the stent structure of FIG. 1.
Figure 4:
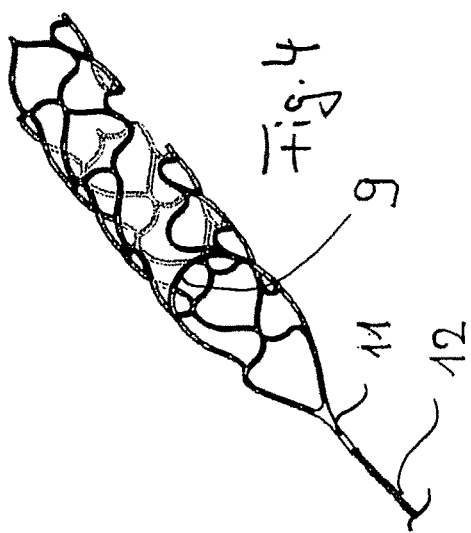

The representation shown in FIGS. 1 and 3 is a planar, two-dimensional representation of a cut-open stent structure 1; and the three-dimensional representations are reflected in FIGS. 2 and 4. In the planar, two-dimensional representation, the meshes 3 immediately adjacent to the meshes 3' in such a manner that it results in an overall tubular structure comprising a slit or channel 7 extending circumferentially roughly half around the shell face 6.

The variants of FIGS. 1 and 3 differ in the shape of the connectors 5 and 5', which in the case of FIG. 3 are configured longer and converged in a coupling element 11 (see FIG. 4). The coupling element 11 may, for example, be an electrolytically corrodible system that permits detaching the stent structure 1 from the guide wire 12 (see FIG. 4). In the variant according to FIG. 2, two detaching elements 6, 6' may be provided for electrolytic detachment.

Both embodiments have in common that the slit 7 is bridged by the dip 9. The clip 9 attaches to the combs lying at the rims 10, 10' of the mesh structure, and with its arch it points to the distal side of the stent structure. This allows for unproblematic pulling-in of the stent structure into a catheter. Together with the adjacent connectors 5 and 5', the tensioning arch 9 forms a capture sling and/or opening of a capture cage converging in the coupling element 11 (FIG. 4). To this effect, the distal end the stent structure may also be occluded with a mesh structure.

In the representations of FIGS. 2 and 4, which are a three-dimensional representation of the stent structures of FIGS. 1 and 3, the webs of the stent structure that lie on the rear side are shown bright. What can be seen here is the slit 7 extending at the proximal end of the structure under the tensioning clip 9 and winding towards the right side around the shell face 8 of the stent structure. The slit 7 terminates in its distal position on the bottom side of the stent structure 1, thus describing a rotation by about 180°.

Figure 5:
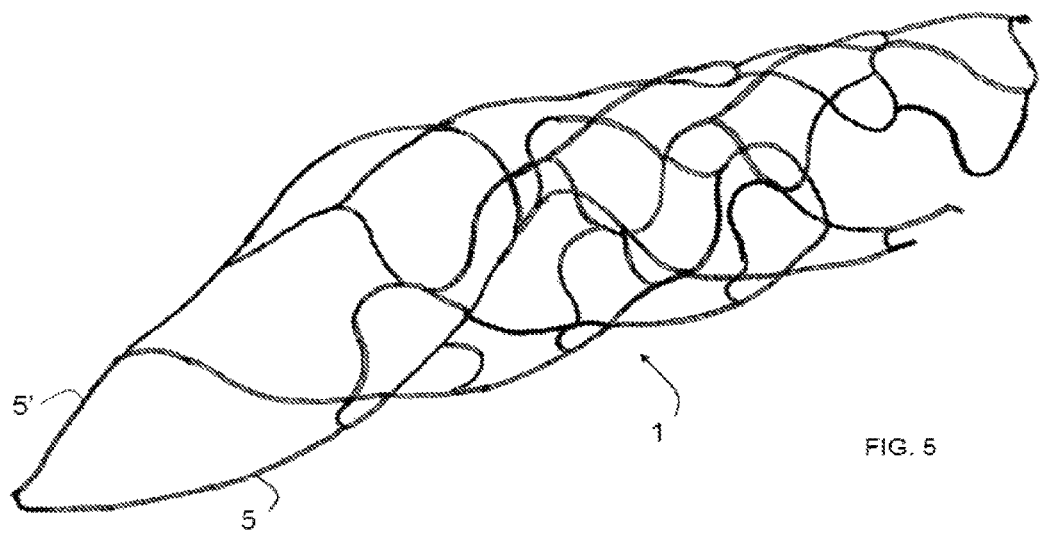
FIG. 5 is a perspective of an inventive stent structure with two connectors.

FIG. 5 shows a three-dimensional representation of an inventive stent structure, wherein the connectors 5 and 5' are provided with inwardly directed hooks engaging into a corresponding take-up of a coupling element 11 of a guide wire 12. As long as the coupling element with the proximal end of the connectors 5 and 5' is located in a catheter, the stent structure 1 is coupled to the guide wire. On pushing it out from the catheter, the connection between the connectors 5, 5' and the coupling element 11 disappears and the structure is released as a stent for retention in the vascular system. The disengagement, however, will occur only in special cases (of emergency), for example if the device cannot be retracted ready into the catheter.

Clearly recognizable in FIG. 5 is the loop-type structure composed of the clip 9 and the connectors 5, 5' as well as the course of webs of the stent structure along the shell face 8 which with their edges serve to take an impact on the thrombus material to be removed and which shear it off from the vessel wall.

Figure 6:
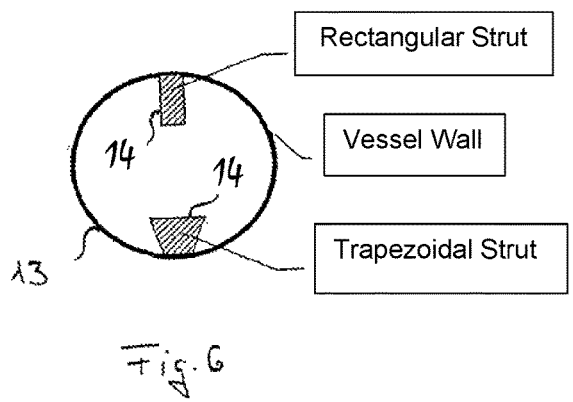
FIG. 6 is a representation of the web cross-sections of the stent structure.

FIG. 6 illustrates these two preferred embodiments of the webs 14 with a rectangular and a trapezoidal cross-section, with the small side each pointing to the shell face 8 of the stent structure 1 and to the vessel wall 13, respectively. These variants ensure the required stability of the mesh net on the one hand and a good shear and displacement effect on the thrombus on the other hand.

Figure 7:
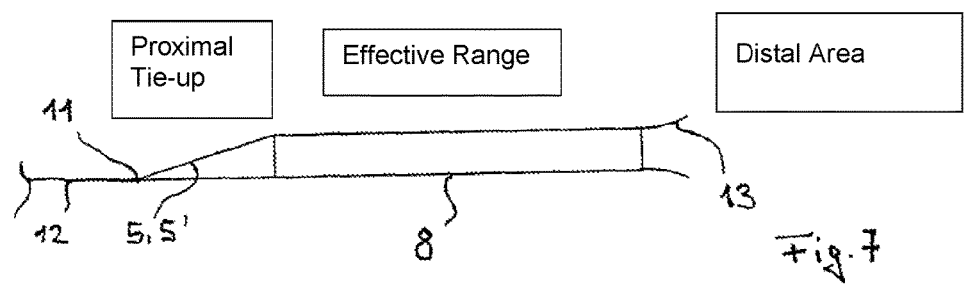
FIG. 7 shows a schematic view of the inventive thrombectomy device.

FIG. 7 schematically shows the set-up of an inventive thrombectomy device comprising the guide wire 12, the coupling element 11, the area of the proximal tie-up to the connectors 5, 5', the effective range with the shell face 8 and the distal area 13 with a trumpet-shaped expansion.

Equal reference numbers in these figures represent equal factual circumstances.

The invention claimed is:

1. A thrombectomy device comprising:
   a substantially cylindrical stent structure (1) comprised of a shell face (8), a plurality of meshes (3, 4) and two connectors (5, 5') that are disposed at different meshes (3) at the proximal end of the stent structure (1), and
   a guide wire (12), which comprises a coupling element (11) to which the connectors (5, 5') are coupled,
   wherein the stent structure is characterized by a continuous slit (7) open at a distal end thereof and which extends helically over and throughout the length of the shell face (8) of the stent structure (1), and a single tensioning clip (9) that continuously spans the slit (7) at the proximal end, the tensioning clip (9) being attached to combs at rims (10, 10') of the mesh structure,
   wherein the tensioning clip forms an arch that points to the distal end of the stent structure, and
   wherein the tensioning clip (9) and the connectors (5, 5') form a loop which converges in the coupling element (11).

2. A device according to claim 1, characterized in that the stent structure comprises a shape-memory material.

3. The device of claim 2, wherein the shape-memory material is Nitinol or a nickel-titanium-chromium alloy.

4. A device as defined in claim 1, characterized in that the stent structure (1) is cut out of a tube and has rectangular or trapezoidal web cross-sections.

5. A device as defined in claim 4, characterized in that the web cross-sections include a small side that forms the shell face (8) of the stent structure (1).

6. A device as defined in claim 1, characterized in that the stent structure (1) is mechanically, hydraulically or electrochemically detachable from the guide wire (12).

7. A device as defined in claim 6, characterized in that the coupling element (11) is configured as a detaching element.

8. A device as defined in claim 6, characterized by two detaching spots.

9. The device of claim 8, with an electrochemical detachment.

10. A device as defined in claim 1, characterized in that the coupling element (11) is peripherally arranged to the connectors.

11. A device as defined in claim 1, characterized in that the distal end of the stent structure (1) is widened-up in a conical or trumpet shape.

12. A device as defined in claim 1 characterized by marker elements.

13. A thrombectomy device comprising:
a substantially cylindrical stent structure (1) comprised of a plurality of meshes (3, 4) and two connectors (5, 5') that are disposed at different meshes (3) at the proximal end of the stent structure (1), and
a guide wire (12), which comprises a coupling element (11) to which the connectors (5, 5') are coupled,
wherein the stent structure is characterized by a continuous slit (7) open at a distal end thereof and which extends helically over the shell face (8) of the stent structure (1), and a tensioning clip (9) that continuously spans the slit (7) at the proximal end, the tensioning clip (9) being attached to combs at rims (10, 10') of the mesh structure,
wherein the tensioning clip forms an arch that points to the distal end of the stent structure, and
wherein the tensioning clip (9) and the connectors (5, 5') form a loop which converges in the coupling element (11).

\* \* \* \* \*